United States Patent [19]

Dove et al.

[11] Patent Number: 4,686,970
[45] Date of Patent: Aug. 18, 1987

[54] DEVICES FOR SPINAL FIXATION

[75] Inventors: John Dove, Stone; Anthony D. Showell, Belbroughton, both of England

[73] Assignee: A. W. Showell (Surgicraft) Limited, Belbroughton, England

[21] Appl. No.: 681,937

[22] Filed: Dec. 14, 1984

[51] Int. Cl.$^4$ .............................................. A61F 5/04
[52] U.S. Cl. ................................. 128/92 YM; 128/69
[58] Field of Search .................. 128/69, 92 B, 92 BC, 128/92 C, 92 D; 623/11, 16, 18-23

[56] References Cited

U.S. PATENT DOCUMENTS

| 4,278,091 | 7/1981 | Borzone | 128/92 B |
| 4,448,191 | 5/1984 | Rodnyansky et al. | 128/69 |
| 4,512,346 | 4/1985 | Lemole | 128/92 |
| 4,573,454 | 3/1986 | Hoffman | 128/92 |
| 4,573,458 | 3/1986 | Lower | 128/92 |
| 4,604,995 | 8/1986 | Stephens et al. | 128/92 |

FOREIGN PATENT DOCUMENTS

| 0048038 | 3/1982 | European Pat. Off. | 128/92 |
| 2807083 | 8/1979 | Fed. Rep. of Germany | 128/92 B |
| 7439762 | 8/1976 | France | 128/92 B |
| 0706080 | 1/1980 | U.S.S.R. | 128/92 B |

OTHER PUBLICATIONS

Herring, John A. and Dennis R. Wenger, 1981, Segmental Spinal Instrumentation, Spine 7(3), 1982, 285-298.

Primary Examiner—Richard J. Apley
Assistant Examiner—David Jlockelle
Attorney, Agent, or Firm—King & Schickli

[57] ABSTRACT

A spinal fixation device (FIG. 1) of the type consisting of rod of biocompatible material (e.g. stainless steel) formed into a rigid rectangle has its shorter sides (11) bent in the same direction from the plane of the longer sides (12) to fit more closely upon the spine than the known flat rectangle, each shorter side (11) having two straight portions (13) at an angle to each other of between 90° and 110°, with a small radius curve (14) between them and small radius curves (15) at the corners formed with the longer sides (12).

A fixation device (FIG. 8) for use on the spine of an infant or juvenile consists of similar rod formed into a rigid U-shape with a base portion (21) similar to the shorter sides (11) of the rectangle, i.e. bent from the plane of the sides (22) of the U, so that when the sides (22) are wired to the spine the wires can slide along the sides (22), to allow for growth of the spine while maintaining support therefor.

7 Claims, 10 Drawing Figures

DEVICES FOR SPINAL FIXATION

This invention relates to devices for spinal fixation, of which one known type consists of stainless steel round rod formed by bending and homogeneously welding into a rectangle adapted to fit neatly on the posterior surface of the spine and embrace two or more bones between its shorter sides with its longer sides substantially parallel to the length of the bones, the rectangle being fixed in place to immobilise the embraced bones with respect to each other by means of wires around or looped through the rectangle and passing through holes in the bones.

The object of the invention is to provide improved devices for spinal fixation.

According to one aspect of the present invention, a device for spinal fixation consists of rod of biocompatible material formed into a rigid rectangle with its shorter sides bent (e.g. into or including a curve) in the same direction from the plane of the longer sides.

The bending (and/or curving) of the shorter sides enables the "roofed" rectangle to fit more closely upon the spine than the previously "flat" rectangle and therefore it appears less bulky. This reduces dead spaces between the device and the spine, thus effectively reducing the risk of haematoma and infection, whilst being biomechanically more efficient. Correct fixing of the "roofed" rectangle is more consistently obtained because wires or other strands looped through the rectangle round the shorter sides are automatically guided down the "slopes" of the shorter sides to rest at the corners formed with the longer sides. Furthermore, because the "roofed" rectangle makes a better fit and affords greater inherent torsional rigidity than a flat rectangle, it gives much greater control of rotation of the immobilised bones with respect to the remainder of the spine.

The "roofed" rectangle is the first implanted device to give the spine effective torsional rigidity, therefore allowing immediate mobilization following surgery, without the need of any external cast or brace.

The shorter sides preferably lie in parallel planes, perpendicular to the plane of the longer sides, and each shorter side preferably has two straight portions, at an angle to each other of between 90° and 110°, with a small radius curve between them and small radius curves at the corners formed with the longer sides. Thus the "roofed" rectangle may be formed of 3/16" diameter stainless steel rod with radiused curves and homogeneously joined, but it may alternatively be formed of titanium rod.

A "roofed" rectangle of appreciable length may be provided with at least one rodar crossbar between the longer sides, the crossbar being bent similarily to the shorter sides and in the same direction. Such a crossbar may have tubular ends slidable along the longer sides, to allow for ajustment to suit intermediate bones.

Any of the sides of the "roofed" rectangle, or a crossbar thereon, may be provided with at least one integral pierced lug or "eye" for a fixation screw or pin.

In addition to providing "roofed" rectangles of different lengths and/or widths, the shorter sides may have different "roof" angles, to suit different sizes of bones and/or bone combinations.

According to another aspect of the present invention, a device for spinal fixation consists of rod of biocompatible material formed into a rigid U-shape with a base portion shorter than parallel sides of the U, and with the base portion bent (e.g. into or including a curve) from the plane of the sides.

The bending (and/or curving) of the base portion of the U enables it to fit closely at one position on a spine of an infant or juvenile and be wired thereto, whilst the sides of the U extend parallel to the spine, which may be wired or tied with other strands slidably thereto, or to at least one crossbar bent (and/or curved) similarly to and in the same direction as the base portion of the U between parallel tubular portions slidable along the sides of the U, to allow for growth of the spine whilst maintaining support therefore.

The base portion of the U preferably has two straight portions at an angle to each other of between 90° and 110° with a small radius curve between them and small radius curves at the corners formed with the sides of the U. Thus the "roofed" U may be formed of 3/16" diameter stainless steel rod with radiussed curves, and has the advantage of not requiring any welding, but it may alternatively be formed of titanium rod.

In addition to providing "roofed" U's of different lengths and/or widths, the base portions may have different "roof" angles, to suit different sizes of bones and/or bone combinations.

Either of the sides or the base of the "roofed" U, or a crossbar slidable thereon, may be provided with at least one integral pierced lug or "eye" for a fixation screw or pin.

A number of embodiments of the invention will now be described, by way of example only, with reference to the accompanying drawings, in which.

Figure 8:
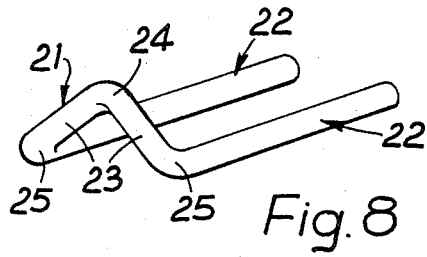
FIG. 8 is a perspective view of a U-shaped spinal fixation device in accordance with the invention.
Figure 9:
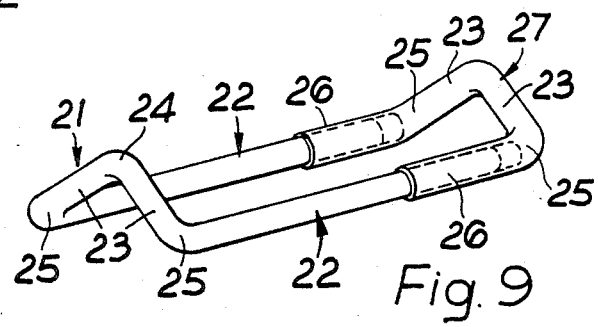
Figure 10:
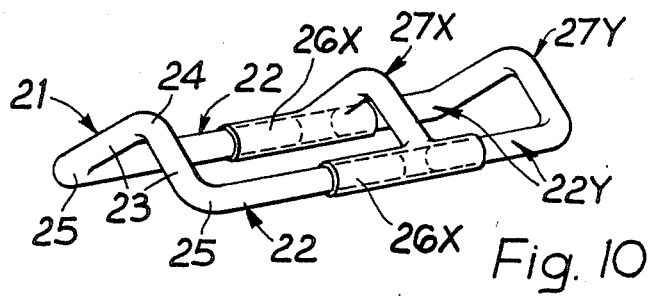

FIG. 9 corresponds to FIG. 8 but shows a U-shaped spinal fixation device provided with an adjustable sliding crossbar; and FIG. 10 also corresponds to FIG. 8 but shows two slidable crossbars.

The spinal fixation devices shown in FIGS. 1 to 5 each consist of rod of biocompatible material (e.g., stainless steel or titanium of 3/16" diameter) formed into a substantially continuous rigid rectangle with its shorter sides 11 bent in the same direction from the plane of the longer sides 12. The shorter sides 11 lie in parallel planes perpendicular to the plane of the longer sides 12, and each shorter side 11 has two straight portions 13 at an angle to each other of 100°, with a small radius curve 14 between them and small radius curves 15 at the corners formed with the longer sides.

The bending and curving of the shorter sides 11 enables such a "roofed" rectangle to fit more closely upon the spine than a "flat" rectangle and therefore it appears less bulky. As will be appreciated from reference to FIGS. 4 and 5 this causes the longer sides 12 of the device to be in contact with the spine, thus reducing dead spaces between the device and the spine, with accompanying reduction in the risk of haematoma and infection. Correct fixing of the "roofed" rectangles is more consistently obtained because wires 16 (or other strands) looped through the rectangle round the shorter sides 11 are automatically guided down the "slopes" 13 of the shorter sides to rest at the corners 15 formed with the longer sides 12. Furthermore, as will also be appreciated from reference to FIGS. 4 and 5, because the "roofed" rectangles make a better fit and afford greater inherent torsional rigidity than flat rectangles, they give much greater control rotation of the immobilized bones with respect to the remainder of the spine.

Figure 3:
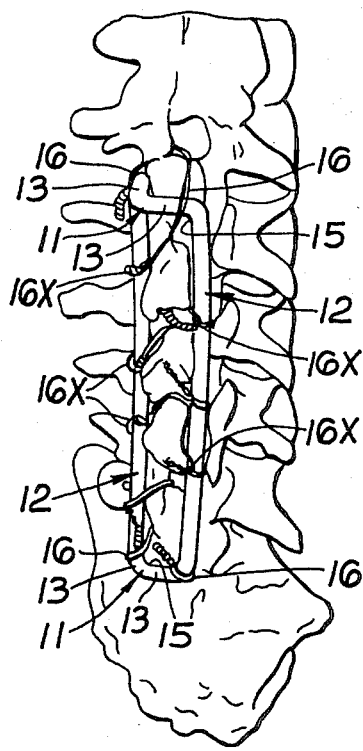
FIG. 3 is a perspective view showing a similar but even longer rectangular spinal fixation device than in FIG. 2 wired in place to the sacrum and adjacent lumbar vertebrae.
Figure 4:
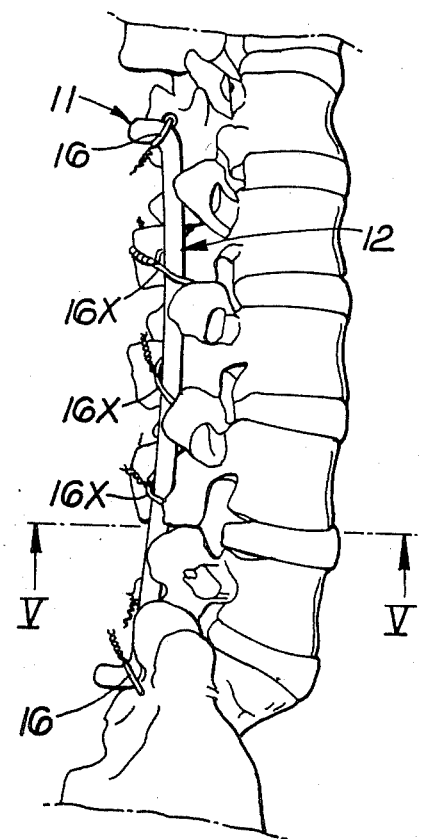
FIG. 4 is a fragmentary side elevation of FIG. 3 to a slightly larger scale.
Figure 5:
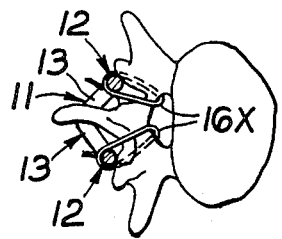
FIG. 5 is a section from the line V—V of FIG. 4.

In FIGS. 3 and 4 the longer sides 12 of the rectangle are shown having been bent to a slight curvature to match the curvature of the spine, and has further wires 16X (or other strands) looped through the rectangle at intermediate positions along the longer sides.

Figure 1:
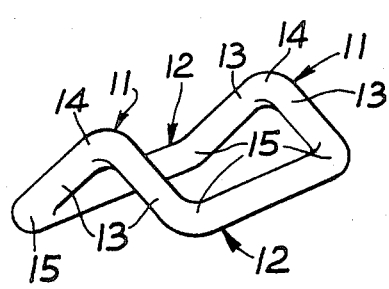
FIGS. 1 and 2 are perspective views of two sizes of rectangular spinal fixation device in accordance with the invention.
Figure 2:
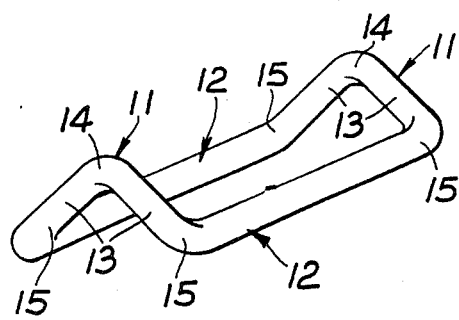
Figure 6:
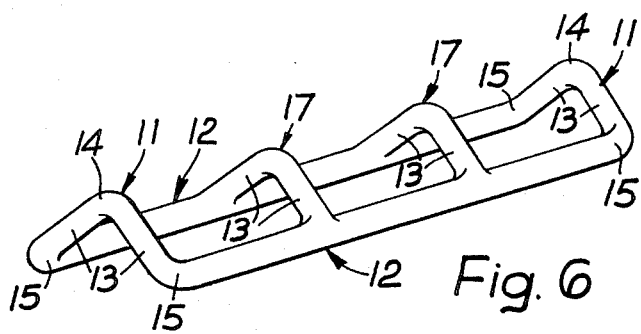
FIG. 6 is a perspective view of another rectangular spinal fixation device in accordance with the invention having two fixed intermediate crossbars.

In FIG. 6 a "roofed" rectangle of greater length than those of FIGS. 1 and 2, and comparable with that of FIGS. 3 and 4, is provided with a pair of fixed rods or crossbars 17 between the longer sides 12, the crossbars being bent similarly to the shorter sides 11 and in the same direction.

Figure 7:
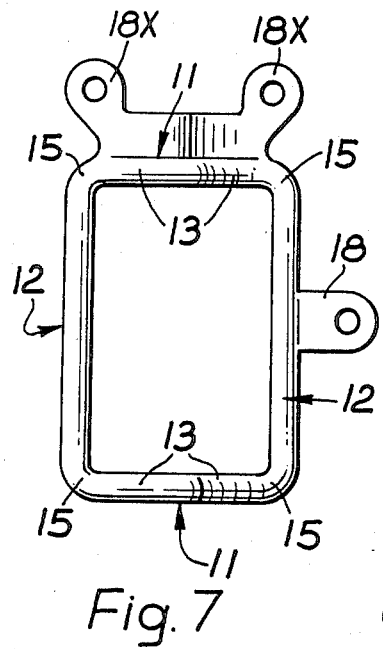
FIG. 7 is a plan of a rectangular spinal fixation device similar to that of FIG. 2 but having integral pierced lugs or "eyes"

The "roofed" rectangle shown in FIG. 7 is similar to that of FIG. 2 but is provided with a pierced lug or "eye" 18 integral with one longer side 12 and a pair of pierced lugs or "eyes" 18X integral with one shorter side, for additional fixing by means of fixation screws or pins (not shown).

The spinal fixation device shown in FIG. 8 consists of rod of biocompatible material (e.g. stainless steel or titanium of 3/16" diameter) formed into a rigid U-shape with a base portion 21 shorter than parallel sides 22 of the U, and with the base portion 21 bent in a plane perpendicular to the plane of the sides 22, with two straight portions 23 at an angle to each other of 100°, with a small radius curve 24 between them and small radius curves 25 at the corners formed with the sides 22.

The bending of the base portion 21 of the U enables it to fit closely at one position on a spine (not shown) of an infant or juvenile and be wired thereto, whilst the sides 22 of the U extend parallel to the spine, being slidably wire thereto to allow for growth of the spine whilst maintaining support therefor.

Alternatively, as shown in FIG. 9, a rodar crossbar 27 bent similarly to and in the same direction as the base portion 21 of the U may be provided between parallel tubular portions 26 slidable along the sides 22 of the U. Or again, as shown in FIG. 10, two slidable crossbars may be provided by having one crossbar 27X provided with tubular portions 26X open at each end, the other crossbar 27Y being formed by a U-shaped member similar to the basic U-shaped fixation device, with the sides 22Y slidable in the opposite ends of the tubular portions 26X to the sides 22 of the basic fixation device.

What we claim is:

1. A device for spinal fixation comprising a rod of biocompatible material formed into a substantially continuous rigid rectangle having integral shorter and longer sides connected together at corners, said shorter sides being bent and extending in the same direction as each other substantially transverse to a plane containing said longer sides, the bending of said shorter sides enabling the receipt of the spine within the device so that said longer sides fit in contact with the spine thereby allowing said rectangle to be secured to the spine by wires with those wires looped around the shorter sides of said rectangle being automatically guided down said shorter sides to rest at the corners connecting said shorter sides with said longer sides.

2. A device as in claim 1, wherein said shorter sides are substantially parallel to each other and substantially perpendicular to said longer sides.

3. A device as in claim 1 wherein each shorter side has two straight portions at an angle to each other of between 90° and 110°, with a small radius curve between them and small radius curves at all the corners formed with the longer sides.

4. A device as in claim 1, provided with at least one additional rod disposed between said longer sides and connected thereto, said additional rod being bent similarly to said shorter sides and in the same direction.

5. A device as in claim 1, wherein said rod formed into a rigid rectangle is provided with at least one integral pierced lug.

6. A device as in claim 1 formed of stainless steel rod.

7. A device as in claim 1 formed of titanium rod.

* * * * *